(12) United States Patent
Lee et al.

(10) Patent No.: US 6,620,930 B1
(45) Date of Patent: Sep. 16, 2003

(54) PROCESS FOR PREPARING 7-AMINO-3-METHOXYMETHYL-3-CEPHEM-4-CARBOXYLIC ACID

(75) Inventors: Gwan-Sun Lee, Seoul (KR); Jae-Heon Lee, Kyungki-do (KR); Young-Kil Chang, Seoul (KR); Chul-Hyun Park, Seoul (KR); Gha-Seung Park, Kyungki-do (KR); Cheol-Kyung Kim, Kyungki-do (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 10/110,162

(22) PCT Filed: Oct. 13, 2000

(86) PCT No.: PCT/KR00/01144

§ 371 (c)(1),
(2), (4) Date: Apr. 4, 2002

(87) PCT Pub. No.: WO01/27117

PCT Pub. Date: Apr. 19, 2001

(30) Foreign Application Priority Data

Oct. 13, 1999  (KR) ......................................... 1999-44322

(51) Int. Cl.$^7$ ................................................ C07D 50/26
(52) U.S. Cl. ..................................................... 540/230
(58) Field of Search .......................................... 540/230

(56) References Cited

U.S. PATENT DOCUMENTS 5,034,521 A * 7/1991 Fukuzaki et al. ............ 540/230
5,451,675 A * 9/1995 Hirayama et al. ........... 540/230

* cited by examiner

*Primary Examiner*—Mark L. Berch
(74) *Attorney, Agent, or Firm*—Anderson Kill & Olick

(57) ABSTRACT

7-amino-3-methoxymethyl-3-cephem-4-carboxylic acid of formula (I) can be easily prepared by reacting 7-aminocephalosporanic acid of formula (II) with an azeotropic mixture of trimethyl borate and methanol in the presence of methanesulfonic acid:

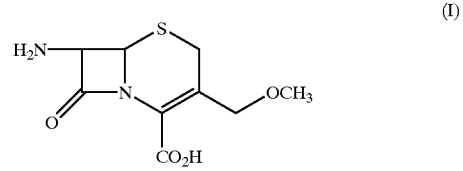

(I)

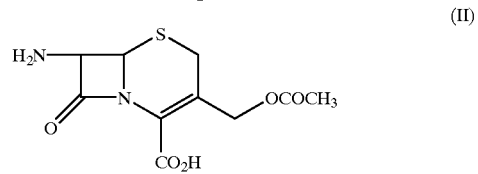

(II)

7 Claims, No Drawings

PROCESS FOR PREPARING 7-AMINO-3-METHOXYMETHYL-3-CEPHEM-4-CARBOXYLIC ACID

FIELD OF THE INVENTION

The present invention relates to a high-yield process for preparing 7-amino-3-methoxymethyl-3-cephem-4-carboxylic acid which is useful intermediate in the preparation of cephalosporin antibiotics.

BACKGROUND OF THE INVENTION 7-amino-3-methoxymethyl-3-cephem-4-carboxylic acid of formula (I) is a precursor of cefpodoxime proxetil, and there have been reported many methods for the preparation thereof starting from 7-aminocephalosphoranic acid(7-ACA) of formula (II).

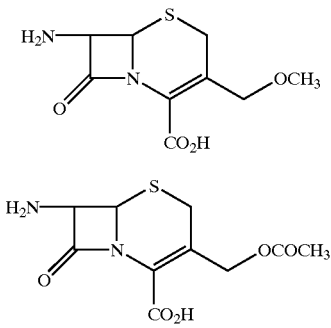

For example, 7-amino-3-methoxymethyl-3-cephem-4-carboxylic acid has been prepared by the steps of protecting the 7-amino group of 7-ACA with a phenylacetyl group; converting the 3-acetoxy group to a methoxy group by the action of methanol-sodium bicarbonate or methanol-calcium chloride; and removing the protection group (see JP Patent No. 82,192,392 and U.S. Pat. No. 4,482,710). However, this method has the problems that yields obtained are very low (approximately less than 20%) and the process requires multi-steps.

JP Patent No. 84,163,387 teaches a method of preparing 7-amino-3-methoxymethyl-3-cephem-4-carboxylic acid by treating 7-aminocephalosporanic acid with methanesulfonic acid-methanol. However, this method also has the problem of low yield (approximately 30%), and the product purity is poor (approximately 30 to 40%) due to the formation of by-products such as lactone or the degradation materials of the β-lactam ring.

Alternatively, 7-amino-3-methoxymethyl-3-cephem-4-carboxylic acid may be obtained by reacting 7-ACA in sulfolane with boron trifluoride-methanol (see EP patent No. 204,657), but this method requires the use of gaseous boron trifluoride which is hazardous and difficult to handle.

EP Patent 262,744 discloses a method of preparing 7-amino-3-methoxymethyl-3-cephem-4-carboxylic acid by reacting 7-ACA with methanol in the presence of a halide of antimony or zinc. However, this method is hampered by the problem of low yield (approximately 40%) and is not suitable for mass production due to the use of column chromatography for separating final product.

Further, 7-amino-3-methoxymethyl-3-cephem-4-carboxylic acid has been prepared by treating 7-aminocephalosporanic acid with boron trifluoride-methanol in the presence of halosulfonic acid or alkylsulfonic acid (See JP Patent No. 88,115,887) or zinc chloride-methanol (See JP Patent No. 89,242,590). These methods give relatively good yields (approximately 60%), but still have the problem of low product purity.

EP patent No. 343,926 teaches a method of preparing 7-amino-3-methoxymethyl-3-cephem-4-carboxylic acid by reacting 7-aminocephalosporanic acid with trimethyl borate in sulfolane, in the presence of sulfuric acid and antimony pentachloride. However, this method requires the use of expensive antimony pentachloride as well as 98% trimethyl borate which is difficult to handle.

EP patent No. 485,204 teaches a method for preparing 7-amino-3-methoxymethyl-3-cephem-4-carboxylic acid by treating 7-ACA in a solution containing an alkoxysulfonic acid with a trialkyl borate and $CH_2(OR)_2$. However, this method still has to deal with the difficulty of handling 98% trimethyl borate and also suffers from the problem of poor process controllability.

Accordingly, there has existed a need to develop an improved method for preparing 7-amino-3-methoxymethyl-3-cephem-4-carboxylic acid.

SUMMARY OF THE INVENTION

It is, therefore, an object of the present invention to provide a high-yield process for preparing 7-amino-3-methoxymethyl-3-cephem-4-carboxylic acid of high purity.

In accordance with the present invention, there is provided a process for preparing 7-amino-3-methoxymethyl-3-cephem-4-carboxylic acid of formula (I) which comprises reacting 7-aminocephalosporanic acid of formula (II) with a trimethyl borate-methanol azeotropic mixture in the presence of methanesulfonic acid:

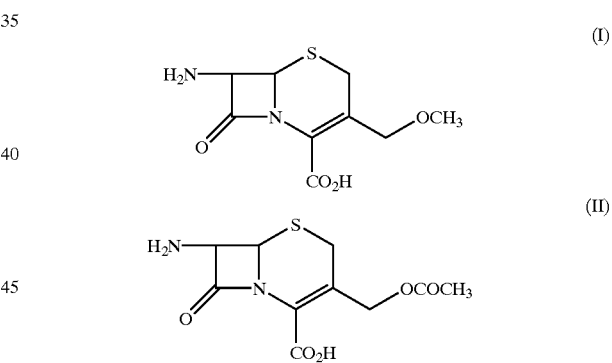

DETAILED DESCRIPTION OF THE INVENTION

The compound of formula (I) may be prepared by reacting 7-aminocephalosporanic acid of formula (II) with a trimethyl borate-methanol azeotropic mixture in the presence of methanesulfonic acid.

In the inventive process, 7-aminocephalosporanic acid may be reacted with methanesulfonic acid and a trimethyl borate-methanol azeotropic mixture in the absence of any added solvent. Methanesulfonic acid may be used in an amount ranging from 5 to 20 equivalents, preferably from 10 to 15 equivalents based on 7-aminocephalosporanic acid.

A trimethyl borate-methanol azeotropic mixture according to the present invention is composed of 70% trimethyl borate and 30% methanol which can be easily formed by an azeotropic distillation and is also commercially available like any other chemicals.

The amount of the trimethyl borate-methanol azeotropic mixture employed in the present invention corresponds to 2.0 to 5.5 equivalents of trimethyl borate and 3.0 to 7.5 equivalents of methanol, based on the amount of 7-aminocephalosporanic acid used.

In the preferred embodiment, the inventive process for preparing the compound of formula (I) may be conducted by (1) dissolving 7-aminocephalosporanic acid in a mixture of methanesulfonic acid and a portion of the azeotropic mixture; and (2) adding the remaining portion of the azeotropic mixture to the solution obtained in step (1).

In step (2), the portion of the trimethyl borate-methanol azeotropic mixture may be added, either dropwise over a period of for 1.5 to 2 hours or in several divided portions at an interval of 20 to 30 minutes, to inhibit the formation of by-products such as lactone or the degradation materials of the β-lactam ring. The amount of the trimethyl borate-methanol azeotropic mixture employed in step (2) is 1.5 to 4.5 equivalents, preferably from 1.8 to 2.6 equivalents of trimethyl borate, and 2.0 to 6.0 equivalents, preferably from 2.5 to 3.7 equivalents of methanol, based on the amount of 7-aminocephalosporanic acid used.

The above reaction in accordance with the present invention may be performed at a temperature ranging from –10 to 40 °C., preferably, from 5 to 15 °C. After adding the trimethyl borate-methanol azeotropic mixture, the reaction is conducted for 1 to 3 hours.

After the completion of the reaction, the pH of the resulting solution is adjusted to 3.0 to 3.5 by using a base to obtain 7-amino-3-methoxymethyl-3-cephem-4-carboxylic acid in a crystalline form. Exemplary bases that may be used in the present invention include alkali metal formates, acetates, bicarbonates and carbonates.

The method of the present invention is very simple and provides 7-amino-3-methoxymethyl-3-cephem-4-carboxylic acid of 97% or higher purity in a yield of greater than 80%.

The following Examples are intended to further illustrate the present invention without limiting its scope; and the experimental methods used in the Examples can be practiced in accordance with the Reference Examples given herein below, unless otherwise stated.

Further, percentages given below for solid in solid mixture, liquid in liquid, and solid in liquid are on the bases of wt/wt, vol/vol and wt/vol, respectively, unless specifically indicated otherwise.

EXAMPLE 1

24.4 ml of methanesulfonic acid was mixed with 6.0 ml of an azeotropic mixture composed of 70% trimethyl borate and 30% methanol and the resulting mixture was cooled to 10° C. 10 g of 7-aminocephalosporanic acid was slowly added thereto and dissolved completely. Then, additional 6.3 ml of the trimethyl borate-methanol azeotropic mixture was added thereto over a period of 1.5 hours while maintaining the temperature at 10° C. and stirred for additional 1.5 hours. 35 ml of cold water was added dropwise to the resulting mixture, and then, 15.6 g of sodium carbonate was carefully added thereto in small portions, followed by adding 100 ml of acetone dropwise thereto.

The resulting mixture was filtered to remove solid sodium methanesulfonate and the filtrate was cooled to 5° C. A solution containing 11.5 g of sodium formate dissolved in 40 ml of water was added dropwise to the filtrate over a period of 1 hour to adjust to pH 3.2. The solid formed was filtered, washed with water and acetone, and then, dried in a vacuum at room temperature to give 7.56 g of 7-amino-3-methoxymethyl-3-cephem-4-carboxylic acid as a pale yellow solid (Yield: 84% and Purity: 97.5%). H-NMR(δ, DMSO-d6): 4.9(dd, 1H), 4.8(dd, 1H), 4.2(s, 2H), 3.4–3.6(q, 2H), 3.2(s, 3H).

EXAMPLE 2

26.8 ml of methanesulfonic acid was mixed with 5.0 ml an azeotropic mixture composed of 70% trimethyl borate and 30% methanol and the resulting mixture was cooled to 10° C. 10 g of 7-aminocephalosporanic acid was slowly added thereto and dissolved completely. Then, additional 10.2 ml of the trimethyl borate-methanol azeotropic mixture was added thereto over a period of 1.5 hours while maintaining the temperature at 10° C. and the mixture was stirred for additional 2 hours. 30 ml of cold water was added dropwise to the resulting mixture, and then, 15.6 g of sodium carbonate was carefully added thereto in small portions, followed by adding 100 ml of acetone dropwise thereto.

The resulting mixture was filtered to remove solid sodium methanesulfonate and the filtrate was cooled to 5° C. A solution containing 13.9 g of sodium acetate dissolved in 50 ml of water was added dropwise thereto to the filtrate over a period of 1 hour to adjust to the pH to 3.5. The solid formed was filtered, washed with water and acetone, and then, dried in a vacuum at room temperature to give 7.38 g of 7-amino-3-methoxymethyl-3-cephem-4-carboxylic acid as a pale yellow solid (Yield: 84% and Purity:

98.2%). H-NMR data was equal to that of the compound prepared in Example 1.

Comparative Example 1

10 g of 7-aminocephalosporanic acid was added to 80 ml of methylene chloride and the resulting mixture was cooled to 0° C., and then, 36.2 m of methanesulfonic acid was added slowly thereto. 7.4 ml of trimethyl borate was added thereto at the above temperature and the resulting mixture was stirred at 0 °C. for 5 hours, and then, the resulting mixture was added to ice-water. The pH of the mixture was adjusted to 3.5 with aqueous ammonia. The ocherous solid formed was isolated by filtration and washed with water. The wet solid was dispersed in water and adjusted the pH to 8 with aqueous ammonia to dissolve the solid in water. Thereafter, the pH of the resulting mixture was adjusted to 3.5 with 3N hydrochloric acid. The resulting mixture was filtered to obtain crystals and the crystals were washed with water and then, dried overnight in a vacuum to give 2.32 g of 7-amino-3-methoxymethyl-3-cephem-4-carboxylic acid as an ocherous solid (Yield: 26% and Purity: 95.5%). H-NMR data was equal to that of the compound prepared in Example 1.

Comparative Example 2

4.1 ml of concentrated sulfuric acid was added to 80 me of sulfolane and the resulting mixture was cooled to about 0° C. 8.2 ml of trimethyl borate was added dropwise thereto and 10 g of 7-aminocephalosporanic acid was added thereto in small portions. 8.4 ml of antimony pentachloride was added dropwise thereto at about 0° C., stirred at 0 °C. for additional 6 hours, and then, the resulting mixture was added to ice-water. The pH of the mixture was adjusted to 3.4 with aqueous ammonia. The ocherous solid formed was isolated by filtration and washed with water. The wet solid was dispersed in water and the pH of the resulting mixture was adjusted to 8 with aqueous ammonia to dissolve the solid in water, and then, the pH of the resulting mixture was adjusted to 3.5 with 3N hydrochloric acid. The resulting mixture was filtered to obtain crystals which were washed with water, and then, dried overnight in a vacuum to give 1.75 g of 7-amino-3-methoxymethyl-3-cephem-4-carboxylic acid as an ocherous solid (Yield: 20% and Purity: 94.3%). H-NMR data was equal to that of the compound prepared in Example 1.

While the embodiments of the subject invention have been described and illustrated, it is obvious that various changes and modifications can be made therein without departing from the spirit of the present invention which should be limited only by the scope of the appended claims.

What is claimed is:

1. A process for preparing 7-amino-3-methoxymethyl-3-cephem-4-carboxylic acid of formula (I) which comprises reacting 7-aminocephalosporanic acid of formula (II) with an azeotropic mixture of trimethyl borate and methanol in the presence of methanesulfonic acid to obtain 7-amino-3-methoxymethyl-3-cephem-4-carboxylic acid of formula (I):

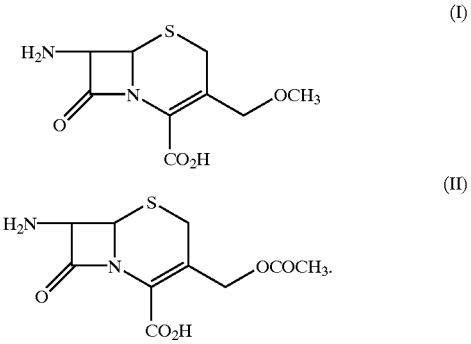

2. The process of claim 1, wherein the amount of methanesulfonic acid is in the range of 5 to 20 equivalents, and the amount of the azeotropic mixture corresponds to 2.0 to 5.5 equivalents of trimethyl borate and 3.0 to 7.5 equivalents of methanol, each based on the amount of 7-aminocephalosporanic acid.

3. The process of claim 1, wherein the azeotropic mixture is composed of 70% by volume of trimethyl borate and 30% by volume of methanol.

4. The process of claim 1, wherein the reaction is carried out at a temperature ranging from −10 to 40° C.

5. The process of claim 1, wherein the reaction is carried out by (1) dissolving 7-aminocephalosporanic acid in a mixture of methanesulfonic acid and a portion of the azeotropic mixture; and (2) adding the remaining portion of the azeotropic mixture to the solution obtained in step (1).

6. The process of claim 5, wherein the amount of the azeotropic mixture used in step (2) corresponds to 1.5 to 4.5 equivalents of trimethyl borate and 2.0 to 6.0 equivalents of methanol, based on the amount of 7-aminocephalosporanic acid.

7. The process of claim 5, wherein the addition of the azeotropic mixture in step(2) is conducted dropwise over a period for 1.5. to 2 hours or portionwise in several divided portions at an interval of 20 to 30 minutes.

* * * * *